(12) United States Patent
Winn

(10) Patent No.: US 11,999,691 B2
(45) Date of Patent: Jun. 4, 2024

(54) ODORLESS ACTIVE AGENTS

(71) Applicant: Actera Ingredients, Inc., Newtown, PA (US)

(72) Inventor: Daniel Winn, Princeton, NJ (US)

(73) Assignee: Actera Ingredients, Inc., Newton, PA (US)

( * ) Notice: Subject to any disclaimer, the term of this patent is extended or adjusted under 35 U.S.C. 154(b) by 0 days.

(21) Appl. No.: 18/258,157

(22) PCT Filed: Dec. 20, 2021

(86) PCT No.: PCT/US2021/064431
§ 371 (c)(1),
(2) Date: Jun. 16, 2023

(87) PCT Pub. No.: WO2022/133354
PCT Pub. Date: Jun. 23, 2022

(65) Prior Publication Data
US 2024/0051912 A1    Feb. 15, 2024

Related U.S. Application Data

(60) Provisional application No. 63/128,094, filed on Dec. 19, 2020.

(51) Int. Cl.
C07C 69/24 (2006.01)
A61K 8/37 (2006.01)
A61Q 7/00 (2006.01)
C07C 69/34 (2006.01)

(52) U.S. Cl.
CPC ............... *C07C 69/24* (2013.01); *A61K 8/37* (2013.01); *A61Q 7/00* (2013.01); *C07C 69/34* (2013.01); *C07C 2601/10* (2017.05)

(58) Field of Classification Search
CPC ..... C07C 69/24; C07C 69/34; C07C 2601/10; C07C 69/44; A61K 8/37; A61Q 7/00; A61Q 5/12
See application file for complete search history.

(56) References Cited

U.S. PATENT DOCUMENTS

| | | |
|---|---|---|
| 4,052,341 A | 10/1977 | Naipawer et al. |
| 9,334,464 B2 | 5/2016 | Bertheir et al. |
| 2010/0105782 A1 | 4/2010 | Bajgrowicz et al. |
| 2017/0360668 A1* | 12/2017 | Brossat .................. A61K 8/492 |
| 2019/0216696 A1 | 7/2019 | Paus et al. |

FOREIGN PATENT DOCUMENTS

WO    2021214205 A1    10/2021

OTHER PUBLICATIONS

Busse, et al., A Synthetic Sandalwood Odorant Induces Wound-Healing Processes in Human Keratinocytes via the Olfactory Receptor OR2AT4, 2014, J Investigative Dermatology, 134:2823-2832.
Pubmed Compound Record for CID 89601295 '[2-Methyl-4(2,2,3-trimethylcyclopent-3-en-1-yl)pent-4-enl] 2-oxo-2-phenylacetate', U.S. Nat'l Library of Med, Feb. 13, 2015, pp. 1-8, (https://pubchem.ncbi.nlm.nih.gov/compound/89601295), p. 2.
Pubmed Compound Record for CID 132190627, '[3,3-dimethyl-4-OXO-5-[(1s)-2,2,3-trimethylcyclopent-3-en-1-yl] acetate', U.S. Nat'l Library of Med, Jan. 29, 2018, pp. 1-9, (https://pubchem.ncbi.nlm.nih.gov/compound/132190627), p. 2.
International Search Report and Written Opinion issued in PCT/US2021/064431, dated Mar. 9, 2022, 8 pages.

* cited by examiner

*Primary Examiner* — Deborah D Carr
(74) *Attorney, Agent, or Firm* — Stinson LLP

(57) ABSTRACT

Disclosed are cyclopentene compounds and compositions containing one or more odorless lipophilic compounds cyclopentene compounds. The compositions can be applied to scalp where they stimulate hair follicles resulting in hair growth and visibly improved human hair.

19 Claims, No Drawings

ODORLESS ACTIVE AGENTS

REFERENCE TO RELATED APPLICATIONS

The present application is the 371 National Stage Application of International Patent Application No. PCT/US2021/064431, filed Dec. 20, 2021, which claims the benefit of U.S. Provisional Application No. 63/128,094, filed Dec. 19, 2020, the entire contents of which are incorporated by reference herein.

FIELD OF THE INVENTION

The present disclosure relates to various compounds, compositions and methods for stimulating hair follicles and hair regrowth with non-odiferous cyclopentene compounds.

BACKGROUND OF THE INVENTION

Hair loss and baldness are signs of aging caused by genetic factors, as well as disease, medication, hormonal treatments, hormonal fluctuations, and psycho-emotional stress. Hair loss can also be caused mechanical and chemical forces on the hair and hair follicle. The latter can occur due to repeated chemical hair process such as oxidative hair color and bleaching, and reductive chemical hair relaxers, which expose the scalp to strong oxidizers and reducing chemicals. Furthermore, excessive braiding, hair extensions and other forceful hair styling activities can pull on and stress the follicle resulting in enhanced hair loss. Premature hair loss can have a debilitating psychological and emotional impact on humans and there is a need in art for more effective pharmaceutical and cosmetic treatments.

BRIEF SUMMARY OF THE INVENTION

Various aspects of the present disclosure are directed to compositions comprising non-odiferous cyclopentene compounds and methods of using these compositions for stimulating hair follicles and hair regrowth.

One aspect is directed to compositions comprising a compound of Formula 1:

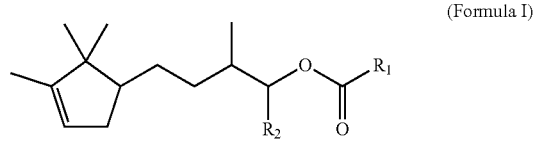

(Formula I)

wherein $R_1$ is substituted or unsubstituted hydrocarbyl having 2-30 carbon atoms and $R_2$ is hydrogen or $C_1$ alkyl.

Another aspect is directed to compositions comprising a compound of Formula II:

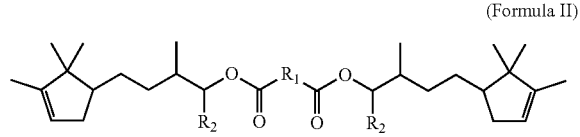

(Formula II)

wherein $R_1$ is substituted or unsubstituted hydrocarbyl having 2-30 carbon atoms and $R_2$ is hydrogen or $C_1$ alkyl.

Other aspects of the present disclosure are directed to methods of stimulating hair follicles and/or promoting hair growth comprising applying the above described compositions topically to a subject in need thereof.

Still further aspects are directed to processes for preparing the compositions.

Other objects and features will be in part apparent and in part pointed out hereinafter.

DETAILED DESCRIPTION OF THE INVENTION

In general, the present disclosure is directed to non-odiferous cyclopentene compounds, compositions comprising non-odiferous cyclopentene compounds, and methods of using these compositions for stimulating hair follicles and hair regrowth.

Certain compounds that stimulate scalp keratinocytes are useful in re-growing lost hair (e.g., sandalore/brahmanol). According to Busse et al., "A Synthetic Sandalwood Odorant Induces Wound-Healing Processes in Human Keratinocytes via the Olfactory Receptor OR2AT4," Journal of Investigative Dermatology, 2014, 134: 2823-2832, certain fragrance cyclopentene compounds that have been identified as agonists of the cutaneous olfactory receptor OR2AT4, and found to induce Ca2+ signals in cultured human keratinocytes. This stimulation of keratinocytes increases cell proliferation and regeneration of keratinocyte. Furthermore, according to US Patent Application US20190216696A1, these cyclopentene fragrance compounds stimulate hair follicles and hair regrowth.

These cyclopentene compounds are odiferous aroma chemical with a strong woody odor, often characterized as similar to sandalwood. Hair and scalp treatments with such compounds result in an unappealing strong woody odor emanating from treatment site. The odiferous cyclopentene compounds draw negative attention to the user and to their scalp. This increases psycho-emotional stress by drawing unwanted attention from hair loss though a strong odor.

It has been discovered that certain non-odiferous cyclopentene compounds that when applied topically stimulate the dermal and scalp and hair follicles, without actually creating odor that is noticeable to human nasal olfactory receptors. The compounds of the function as prodrugs of sandalore/brahmanol where enzymes on the skin (scalp) break the ester bond and release the drug.

Active Agents

The present disclosure provides for hair growth active agents. The hair growth active agents are alkyl and alkenyl carboxylic acid esters of cyclopentene alcohol compounds such as sandalore (also known as sandal pentanol) and brahmanol. They can comprise the compounds of Formula I:

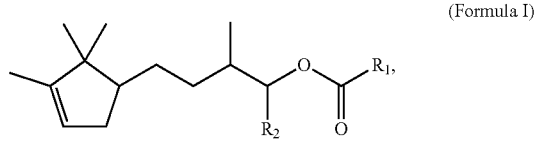

(Formula I)

where $R_1$ is substituted or unsubstituted hydrocarbyl having two carbon atoms or more and $R_2$ is hydrogen or $C_1$ alkyl (e.g., methyl). The hydrocarbyl can be branched or linear, saturated or unsaturated. In various embodiments, $R_1$ a saturated or unsaturated, linear or branched, aliphatic hydrocarbyl group. Preferably, $R_1$ is a substituted or unsubstituted branched or linear alkyl or alkenyl having 2 or more carbon atoms, such as $C_2$-$C_{30}$, $C_2$-$C_{20}$, or $C_2$-$C_{15}$ alkyl or alkenyl groups. When $R_1$ is alkenyl, the substituent has at least one double bond, but can optionally have two or more double bonds. Examples of acceptable hydrocarbyl groups ($R_1$) include $C_6$ to $C_{22}$ alkyl or alkenyl groups. Among them $C_6$ to $C_{16}$ alkyl is preferable.

As noted, the alkyl ester chain of the active agent ($R_1$) will be at least 2 carbons long or more, branched or linear, saturated or unsaturated. The alkyl ester chain may also be derived from a dicarboxylic acid such as adipic acid, succinic acid, azelaic acid, sebacic acid, and dimer acid, as well us unsaturated di-acids such as maleic acid and itaconic acid. The alkyl ester chain or diester chain is preferably one that that is soluble in an oil phase and is mutually soluble with lipophilic emollients typically used in topical skin and hair products. Preferred alkyl ester chains include those derived from hexanoic acid, octanoic acid, decanoic acid, lauric acid, myristic acid, palmitic acid, stearic acid, behenic acid.

Examples of these esters according to Formula I comprise the following structures:

3-trimethylcyclopent-3-en-1-yl)pentan-2-yl dodecanoate). Most preferably, the ester of Formula I is sandal pentanol caprylate.

Diesters of Formula I are also envisioned where a dicarboxylic acid links two moieties of Formula I via ester linkages. These diesters can be represented by Formula II:

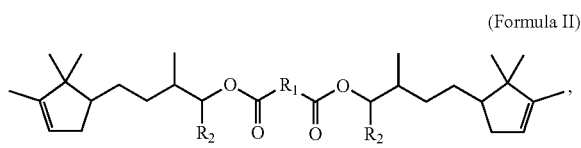

(Formula II)

where $R_1$ is substituted or unsubstituted hydrocarbyl having two carbon atoms or more and each $R_2$ is hydrogen or $C_1$ alkyl (e.g., methyl). The hydrocarbyl can be branched or linear, saturated or unsaturated. In various embodiments, $R_1$ a saturated or unsaturated, linear or branched, aliphatic hydrocarbyl group. Preferably, $R_1$ is a substituted or unsubstituted branched or linear alkyl

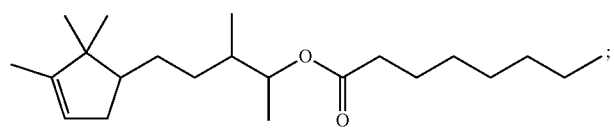

(3-methyl-5-(2,2,3-trimethylcyclopent-3-en-1-yl)pentan-2-yl octanoate)

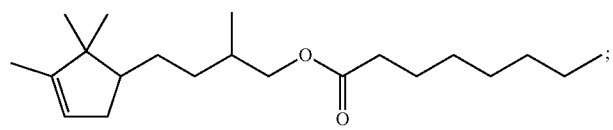

(2-methyl-4-(2,2,3-trimethylcyclopent-3-en-1-yl)butyl octanoate)

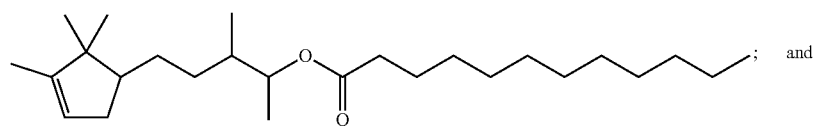

; and (3-methyl-5-(2,2,3-trimethylcyclopent-3-en-1-yl)pentan-2-yl dodecanoate)

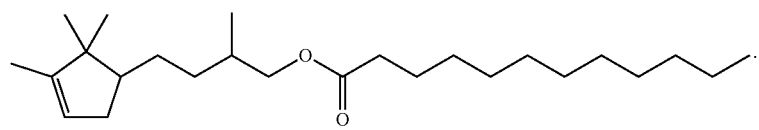

(2-methyl-4-(2,2,3-trimethylcyclopent-3-en-1-yl)butyl dodecanoate)

Preferably, the ester of Formula I is sandal pentanol caprylate (also described above as 3-methyl-5-(2,2,3-trimethylcyclopent-3-en-1-yl)pentan-2-yl octanoate) or sandal pentanol laurate (also described above as 3-methyl-5-(2,2, or alkenyl having 2 or more carbon atoms, such as $C_2$-$C_{30}$, $C_2$-$C_{20}$, or $C_2$-$C_{15}$ carbon chain. When $R_1$ is alkenyl, the substituent has at least one double bond, but can optionally have two or more double bonds.

Examples of the diesters according to Formula II comprise the following structures:

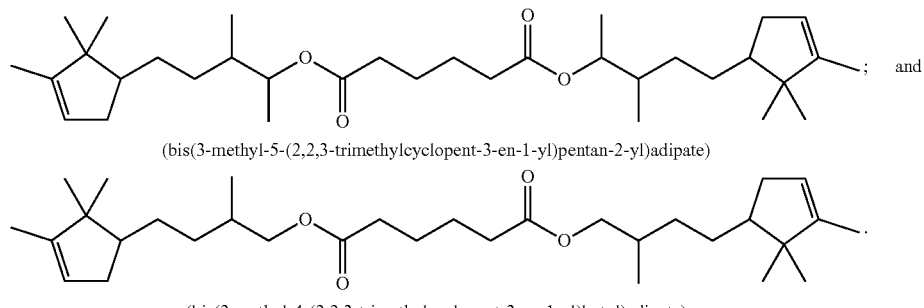

(bis(3-methyl-5-(2,2,3-trimethylcyclopent-3-en-1-yl)pentan-2-yl)adipate)

(bis(2-methyl-4-(2,2,3-trimethylcyclopent-3-en-1-yl)butyl)adipate)

The active agents can be lipophilic with a molecular weight typically greater than 250 Daltons, and are polar due to one or more ester bonds. As a result of this high molecular weight and polar ester structure, these active agents do not stimulate human nasal olfactory sense and have no noticeable smell.

Compositions

Further disclosed are compositions comprising one or more active agents described above. As the active agents do not stimulate human nasal olfactory sense and have no noticeable smell, the compositions can have the same properties.

In various embodiments, the compositions are anhydrous.

In various embodiments, the compositions described herein further comprise a solvent. For example, the solvent can comprise an aqueous solvent (e.g., the solvent can comprise, consist essentially of (e.g., water is 95 wt. % or more, or even 99 wt. % or more of the solvent), or consist of water).

In various embodiments, the present disclosure directed to compositions comprising a compound of formula (I), as described herein, and water. In some embodiments, the composition is homogenously dissolved or dispersed in the water. The water can be distilled water, purified water, spring water, coconut water, thermal water, alkaline water, infused water and/or drinking water.

In various embodiments, the composition has a concentration of water that is about 10 wt. % or greater, about 20 wt. % or greater, about 30 wt. % or greater, about 40 wt. % or greater, about 50 wt. % or greater, about 60 wt. % or greater, about 70 wt. % or greater, about 80 wt. % or greater, or about 90 wt. % or greater. In various embodiments, the composition has a concentration of water that is from about 10 wt. % to about 95 wt. %, from about 10 wt. % to about 90 wt. %, from about 10 wt. % to about 80 wt. %, from about 10 wt. % to about 70 wt. %, from about 10 wt. % to about 60 wt. %, from about 10 wt. % to about 50 wt. %, from about 10 wt. % to about 40 wt. %, from about 10 wt. % to about 30 wt. %, from about 10 wt. % to about 20 wt. %, from about 20 wt. % to about 95 wt. %, from about 20 wt. % to about 90 wt. %, from about 20 wt. % to about 80 wt. %, from about 20 wt. % to about 70 wt. %, from about 20 wt. % to about 60 wt. %, from about 20 wt. % to about 50 wt. %, from about 20 wt. % to about 40 wt. %, from about 20 wt. % to about 30 wt. %, from about 30 wt. % to about 95 wt. %, from about 30 wt. % to about 90 wt. %, from about 30 wt. % to about 80 wt. %, from about 30 wt. % to about 70 wt. %, from about 30 wt. % to about 60 wt. %, from about 30 wt. % to about 50 wt. %, or from about 30 wt. % to about 40 wt. %.

In various embodiments, the composition has a concentration of the compound (i.e., of Formula I or Formula II) that is about 50 wt. % or less, about 40 wt. % or less, about 30 wt. % or less, about 20 wt. % or less, about 10 wt. % or less, about 5 wt. % or less, or about 1 wt. % or less. In some embodiments, the composition has a concentration of the compound that is from about 0.001 wt. % to about 50 wt. %, from about 0.001 wt. % to about 40 wt. %, from about 0.001 wt. % to about 30 wt. %, from about 0.001 wt. % to about 20 wt. %, from about 0.001 wt. % to about 10 wt. %, from about 0.001 wt. % to about 5 wt. %, from about 0.01 wt. % to about 50 wt. %, from about 0.01 wt. % to about 40 wt. %, from about 0.01 wt. % to about 30 wt. %, from about 0.01 wt. % to about 20 wt. %, from about 0.1 wt. % to about 10 wt. %, from about 0.1 wt. % to about 5 wt. %, from about 0.1 wt. % to about 50 wt. %, from about 0.1 wt. % to about 40 wt. %, from about 0.1 wt. % to about 30 wt. %, from about 0.1 wt. % to about 20 wt. %, from about 0.1 wt. % to about 10 wt. %, from about 0.1 wt. % to about 5 wt. %, from about 1 wt. % to about 50 wt. %, from about 1 wt. % to about 40 wt. %, from about 1 wt. % to about 30 wt. %, from about 1 wt. % to about 20 wt. %, from about 1 wt. % to about 10 wt. %, or from about 1 wt. % to about 5 wt. %. Preferably, the composition can have a concentration of the compound that is from about 2 wt. % to about 5 wt. %.

In various embodiments, the compositions described herein can have a pH of about 7 or less, about 6.5 or less, about 6 or less, about 5.5 or less, about 5 or less, about 4.5 or less, about 4 or less, or about 3 or less. In some embodiments, the compositions described herein can have a pH of from about 3 to about 7, from about 3 to about 6, from about 3 to about 5, from about 3 to about 4, from about 4 to about 7, from about 4 to about 6, or from about 4 to about 5.

The compositions described herein may further comprise one or more additives (e.g., cosmetically acceptable ingredients). Examples of cosmetically acceptable ingredients are those listed in the International Cosmetic Ingredient Dictionary and Handbook and those listed in the United States Pharmacopeia. Cosmetically acceptable ingredients include, but are not limited to preservatives, antioxidants, chelating agents, sunscreen agents, vitamins, dyes, hair coloring agents, proteins, amino acids, natural extracts such as plant extracts, humectants, fragrances, perfumes, oils, emollients, lubricants, butters, penetrants, thickeners, viscosity modifiers, polymers, resins, hair fixatives, film formers, surfactants, detergents, emulsifiers, opacifying agents, volatiles, propellants, liquid vehicles, carriers, salts, pH adjusting agents (e.g., citric acid), neutralizing agents, buffers, hair conditioning agents, anti-static agents, anti-frizz agents, anti-dandruff agents, absorbents, and combinations thereof.

For example, surfactants include various anionic, cationic, nonionic, and amphoteric surfactants. Anionic surfactants include, but are not limited to, those containing carboxylate, sulfonate and sulfate ions. Examples of anionic surfactants include sodium, potassium, ammonium of long chain alkyl sulfonates and alkyl aryl sulfonates. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine. Emollients include, for example, silicone compounds, polyols (e.g., propanediol), and triglycerides Emulsifiers include, but are not limited to, copolymers of an unsaturated ester and styrene sulfonate monomer, cetearyl alcohol, glyceryl ester, polyoxyethylene glycol ether of cetearyl alcohol, stearic acid, polysorbate-20, ceteareth-20, lecithin, glycol stearate, polysorbate-60, polysorbate-80, and combinations thereof.

Preservatives include, but are not limited to, glycerin containing compounds, benzyl alcohol, parabens, sodium benzoate, ethylenediamine-tetraacetic acid (EDTA), potassium sorbate, and so on. Antioxidants include, for example, tocopheryls, BHT, ascorbic acid, *Camellia sinensis* leaf extract, ascorbyl palmitate, magnesium ascorbyl phosphate, carotenoids, resveratrol, triethyl citrate, arbutin, kojic acid, tetrahexydecyl ascorbate, superoxide dismutase, zinc, sodium metabisulfite, lycopene, ubiquinone, and combinations thereof.

Conditioning agents include, for example, silicone-based agents, panthenol, hydrolyzed wheat and/or soy protein, amino acids, rice bran wax, meadowfoam seed oil, mango seed oil, grape seed oil, jojoba seed oil, sweet almond oil, hydroxyethyl behenamidopropyl dimonium chloride, aloe leaf extract, aloe barbadensis leaf juice, phytantriol, panthenol, retinyl palmitate, behentrimonium methosulfate, cyclopentasiloxane, quaternium-91, stearamidopropyl dimethylamine, and combinations thereof.

Viscosity modifying agents include, for example, viscous liquids, such as polyethylene glycol, semisynthetic polymers, cellulose derivatives, synthetic polymers, naturally occurring polymers, bentonite, colloidal silicon dioxide, and microcrystalline cellulose, and salts, such as sodium chloride, and combinations thereof.

Opacifying agents include, but are not limited to, glycol distearate and ethoxylated fatty alcohols.

In some embodiments, the compositions described herein comprise at least one of a viscosity modifier (e.g., xanthan gum or equivalent), a preservative (e.g., phenoxyethanol), an emollient (e.g., propanediol), a conditioning agent (e.g., stearamidopropyl dimethylamine, behentrimomium methosulfate, and/or sunflower oil), or an emulsifier (e.g., cetearyl alcohol). In certain embodiments, the composition comprises itaconic acid, arginine, cetearyl alcohol, behentrimonium methosulfate, stearamidopropyl dimethylamine, sunflower oil, xanthan gum, propanediol, and phenoxyethanol.

The present disclosure also comprises solutions of the active agent in cosmetically acceptable oils and emollients. This include but are not limited to emollient esters, polyesters, polyol esters, guerbet esters, fatty alcohol, vegetable waxes, triglycerides, vegetable oils, hydrocarbon fluids such as mineral oils, petrolatum, alkanes and isoalkanes, silicones, and other topical lipophilic emollients known in the art. The lipophilic solutions will include the active agent in an amount necessary to achieve hair follicle stimulation when applied topically to the scalp The present disclosure further comprises other external compositions containing the active agent dispersed in a physiologically acceptable topical formulation, intended to be applied to human skin to stimulate hair follicles and hair growth.

The compositions can be formulated in various suitable forms including, for example, low to moderate viscosity liquids, lotions, milks, mousses, sprays, gels, creams, shampoos, conditioners, roll-on treatments, and the like. Preferably, the compositions described herein are formulated as a roll-on treatment, hair milk, or conditioning mask.

The roll-on treatment formulation preferably comprises triethyl citrate and sandal pentanol caprylate. More preferably, the roll-on treatment comprises about 95% triethyl citrate and about 5% sandal pentanol caprylate.

The hair milk formulation preferably comprises water, sandal pentanol caprylate, olive oil polyglyceryl-6 esters, and phenoxyethanol. More preferably, the hair milk formulation comprises about 85% water, about 2% sandal pentanol caprylate, about 12% olive oil polyglyceryl-6 esters, and about 1% phenoxyethanol.

The conditioning mask formulation preferably comprises water, behentrimonnium methosulfate, cetearyl alcohol, sandal pentanol caprylate, sunflower oil, steramodopropyl dimethylamine, and phenoxyethanol. More preferably, the conditioning mask formulation comprises about 80.5% water, about 3% behentrimonnium methosulfate, about 9% cetearyl alcohol, about 2% sandal pentanol caprylate, about 3% sunflower oil, about 1.5% steramodopropyl dimethylamine, and about 1% phenoxyethanol.

All percentages are by weight of the total composition unless specifically stated otherwise. When more than one composition is used during a treatment, the total weight to be considered is the total weight of all the compositions applied on hair simultaneously (i.e. the weight found "on head") unless otherwise specified. All ratios are weight ratios unless specifically stated otherwise.

Processes of Preparing the Compositions

Esterification of the cyclopentene alcohols can be accomplished by processes known in the art. The cyclopentene alcohol (sandalore or brahmanol) and carboxylic acid can be added in stoichiometric quantities, and esterification catalysts, such as sulfonic acids and organo-tin catalysts can be used to increase the rate of reaction, while the water of reaction can be removed by a reflux condenser. Alternatively, acyl acid chloride (also called alkyl acid chloride) can used instead of the carboxylic acid and the reaction can proceed rapidly without the need for catalysts. For example, sandalore can be reacted with lauryl chloride in a suitable solvent to produce sandalore lauryl esters.

Methods of Use

The present disclosure further relates to external compositions comprising compounds of Formulas I and/or II intended to treat the skin or scalp, to stimulate keratinocytes, to stimulate hair follicles, to improve the condition of skin or hair, to reverse the effects of aging and inflammation on skin and scalp, and to reverse or reduce the impact of hair loss of excessive hair shedding. Said external compositions are particularly distinct because sandalore and brahmanol esters are fully soluble in the oil phase and are free of the characteristic odor of sandalore and brahmanol. Furthermore, the sandalore and brahmanol esters have light emollient feel and provide and added sensory skin-feel benefit to external compositions.

The sandalore and brahmanol esters herein may be combined in an external composition with other ingredients intended to heal or reverse the effects of skin aging, or to heal and reverse excessive hair loss. Examples of said ingredients include, but are not restricted to ascorbic acid and derivatives thereof, ferulic acid, azelaic acid, kojic acid, mandelic acid, alpha-hydroxy acids, beta-hydroxy acids, fruit acids, gluconolactone, heparan sulfate, arbutin, niacinamide, resveratrol, hydroquinone, exfoliants, keratolytics, plant extracts, marine extracts, ferment extracts, isoflavones, peptides, retinol and other retinoids, vitamins, amino acids, biotin, ketoconazole, finasteride, minoxidil, clascoterone, and topical antiandrogens.

In various embodiments of the method, the compound or composition comprising the compound is applied to an external surface of a subject. Preferably, the external surface of the subject comprises hair follicles, such as the scalp. The composition can be applied by being sprayed on, rolled-on, pressed on, rubbed in, or combinations thereof.

In further embodiments of the method, the compound or composition comprising the compound is applied to an external surface of the subject at least one time per day, at least two times per day, at least three times per day, at least four times per day, from about one to three times per day, from about one to two times per day, or one time per day. The compound or composition comprising the compound after application can be left in or removed. The compound or composition comprising the compound can be washed out about 1 minute, about 5 minutes, about 10 minutes, about 15 minutes, about 20 minutes, or about 30 minutes after application.

The subject can be a human or other mammal. The subject is preferably a human.

Definitions

The term "substituted" as used herein, refers to chemically acceptable functional substituent groups, preferably moieties that does not negate the activity of the compounds. Such substituents include, but are not limited to alkyl groups, alkenyl groups, hydroxy groups, oxo groups, alkoxy groups, and/or cycloalkyl groups.

As used herein, the term "hydrocarbyl" refers to hydrocarbyl moieties, unless otherwise specified, preferably containing, 1 to about 50 carbon atoms, preferably 1 to about 30 carbon atoms, and even more preferably 1 to about 18 carbon atoms, including branched or unbranched, and saturated or unsaturated species. Hydrocarbyl groups can be selected from the group consisting of alkyl, alkenyl, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl, heteroarylalkyl, and the like. A hydrocarbyl may be optionally substituted hydrocarbyl. Hence, various hydrocarbyls can be further selected from substituted alkyl (e.g., cyano), substituted cycloalkyl and the like.

The term "alkenyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups can be unsubstituted or substituted by one or more suitable substituents, as defined above.

The term "alkyl," as used herein, refers to a linear or branched hydrocarbon radical, preferably having 1 to 32 carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons). Alkyl groups include, but are not limited to, methyl, ethyl, n-propyl, isopropyl, n-butyl, iso-butyl, secondary-butyl, and tertiary-butyl. Alkyl groups can be unsubstituted or substituted by one or more suitable substituents, as defined above.

The term "alkoxy," as used herein, refers to an alkyl group, as defined herein, appended to the parent molecular moiety through an oxygen atom.

The term "aryl," as used herein, means monocyclic, bicyclic, or tricyclic aromatic radicals such as phenyl, naphthyl, tetrahydronaphthyl, indanyl and the like; optionally substituted by one or more suitable substituents, preferably 1 to 5 suitable substituents, as defined above.

The term "cycloalkyl," as used herein, refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups can be unsubstituted or substituted by one or more suitable substituents, preferably 1 to 5 suitable substituents, as defined above.

The term "hydroxy," as used herein, refers to an —OH group.

The term "oxo," as used herein, refers to a double bonded oxygen (=O) radical wherein the bond partner is a carbon atom. Such a radical can also be thought as a carbonyl group.

Having described the invention in detail, it will be apparent that modifications and variations are possible without departing from the scope of the invention defined in the appended claims.

EXAMPLES

The following non-limiting examples are provided to further illustrate the present invention.

Example 1: Synthesis of Sandalore Caprylate (Sandal Pentanol Caprylate)

Sandalore caprylate ester was prepared according to the following steps:
1. A 3-neck 5 L round bottom flask was charged with a mechanical stirrer and a dropping funnel.
2. 871 g of sandalore, 439 g of triethylamine and 2.5 L ethyl acetate was added to the flask.
3. The flask was placed in ice/water bath. The stirrer is turned on and agitate the mixture for 1 hour.
4. At 0° C., 708 g of octanoyl chloride was added dropwise into the flask.
5. The reaction mixture was slowly warmed to room temperature and keep stirring.

6. The reaction is monitored by TLC. When reaction is done, water was added to quench the reaction.
7. The reaction mixture is washed with water 3 times, dried with $Na_2SO_4$ and concentrated to give final product.

Example 2: Synthesis of Sandalore Laurate (Sandal Pentanol Laurate)

Sandalore laurate ester was prepared according to the following steps:
1. A 3-neck 5 L round bottom flask was charged with a mechanical stirrer and a dropping funnel.
2. 871 g of sandalore, 439 g of triethylamine and 2.5 L ethyl acetate was added to the flask.
3. The flask was placed in ice/water bath. The stirrer is turned on and agitate the mixture for 1 hour.
4. At 0° C., 708 g of dodecanoyl chloride was added dropwise into the flask.
5. The reaction mixture was slowly warmed to room temperature and keep stirring.
6. The reaction is monitored by TLC. When reaction is done, water was added to quench the reaction.
7. The reaction mixture is washed with water 3 times, dried with $Na_2SO_4$ and concentrated to give final product.

Example 3: Anhydrous External Composition

An anhydrous external composition is prepared by mixing one or more of the esters prepared in Examples 1 or 2 with other formulation ingredients.

For roll-on treatment, the procedure is to combine ingredients (triethyl citrate 95%, sandal pentanol caprylate 5%) and mix until uniform. The instructions for use are to apply to the scalp every day for 3-6 months and rub it in if necessary.

Example 4: Micro-Emulsion External Composition

A micro-emulsion external composition is prepared by mixing one or more of the esters prepared in Examples 1 or 2 with other formulation ingredients.

For a hair milk formulation, the ingredients are: water 85%, sandal pentanol caprylate 2%, olive oil polyglyceryl-6 esters 12%, and phenoxyethanol 1%. To prepare the formulation, the ingredients are combined and mixed until uniform. The instructions for use are to spray directly onto the scalp while hair is wet or dry, combing through the hair if necessary, and using daily for at least 3-6 months.

Example 5: Emulsion External Composition

An emulsion external composition is prepared by mixing one or more of the esters prepared in Examples 1 or 2 with other formulation ingredients.

For a conditioning mask, the ingredients are: water 80.5%, behentrimonnium methosulfate 3%, cetearyl alcohol 9%, sandal pentanol caprylate 2%, sunflower oil 3%, stearamodopropyl dimethylamine 1.5%, and phenoxyethanol 1%. To prepare the formulation, combine ingredients, heat to 80 degrees C., and mix until uniform. Then begin cooling to room temperature with continued mixing. The instructions for use are: after shampooing, apply to scalp and hair and allow to sit on scalp for at least 5 minutes, using daily or whenever hair is washed.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions, methods, and processes without departing from the scope of the invention, it is intended that all matter contained in the above description shall be interpreted as illustrative and not in a limiting sense.

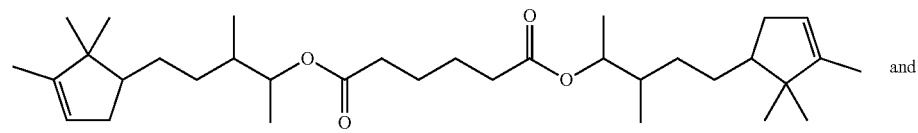

-continued
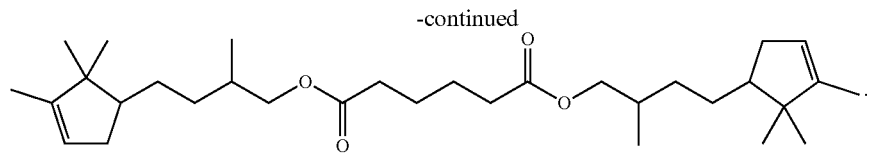

The invention claimed is:

1. A compound of Formula 1:

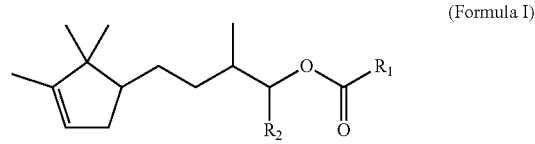

(Formula I)

wherein $R_1$ is substituted or unsubstituted alkyl or alkenyl having 2 to 30 carbon atoms and $R_2$ is hydrogen or $C_1$ alkyl, wherein substituents on the substituted alkyl or alkenyl are selected from the group consisting of hydroxy and alkoxy.

2. A compound of Formula II:

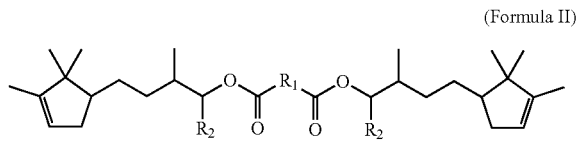

(Formula II)

wherein $R_1$ is substituted or unsubstituted alkyl or alkenyl having 2 to 30 carbon atoms and each $R_2$ is hydrogen or $C_1$ alkyl, wherein substituents on the substituted alkyl or alkenyl are selected from the group consisting of hydroxy and alkoxy.

3. The compound of claim 1, wherein $R_2$ is hydrogen.

4. The compound of claim 1, wherein $R_2$ is methyl.

5. The compound of claim 1, wherein $R_1$ is $C_6$ to $C_{16}$ alkyl.

6. The compound of claim 1, wherein the $R_1$ alkyl or alkenyl is linear or branched.

7. The compound of claim 1, wherein the $R_1$ alkyl or alkenyl has 6 to 16 carbon atoms.

8. The compound of claim 1, wherein the compound is selected from the group consisting of:

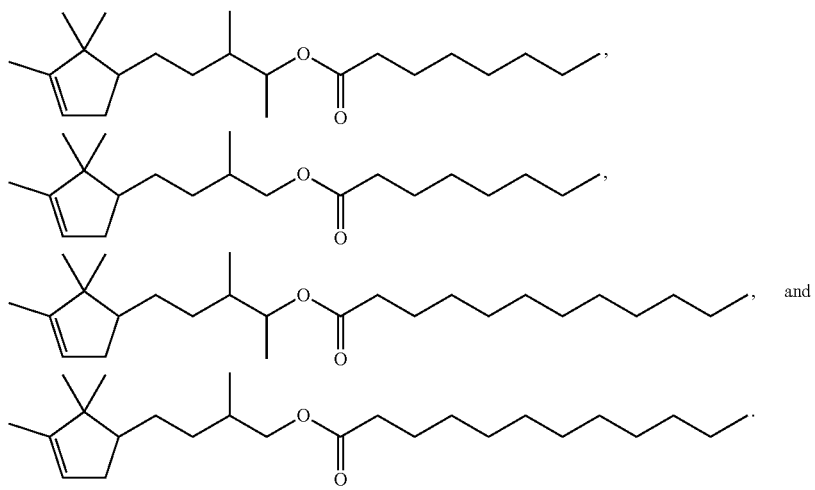

9. The compound of claim 1, wherein the compound is

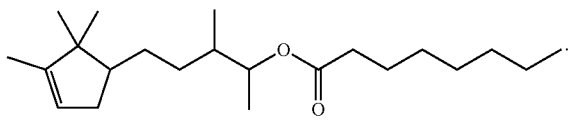 [SMILES: CCCCCCCC(=O)OC(C)C(C)CCC1CC=C(C)C1(C)C]

10. The compound of claim 1, wherein the compound is free from the odor of sandalwood or brahmanol.

11. The compound of claim 1, wherein the compound is free from any noticeable smell.

12. A composition comprising at least one compound of Formula I (Formula I)

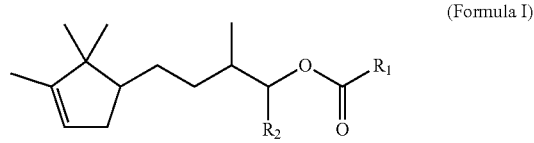

and/or Formula II (Formula II)

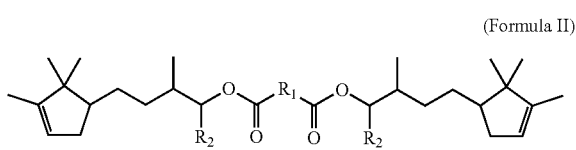

wherein $R_1$ is substituted or unsubstituted alkyl or substituted or unsubstituted alkenyl having 2 to 30 carbon atoms and each $R_2$ is hydrogen or $C_1$ alkyl, wherein substituents on the substituted alkyl or substituted alkenyl are selected from the group consisting of hydroxy and alkoxy.

13. The composition of claim 12, wherein the composition further comprises a cosmetically acceptable ingredient.

14. The composition of claim 12, wherein the composition is formulated as a roll-on treatment, hair milk, or conditioning mask.

15. The composition of claim 12, wherein the composition comprises about 95% triethyl citrate and about 5% sandal pentanol caprylate.

16. The composition of claim 12, wherein the composition comprises about 85% water, about 2% sandal pentanol caprylate, about 12% olive oil polyglyceryl-6 esters, and about 1% phenoxyethanol.

17. The composition of claim 12, wherein the composition comprises about 80.5% water, about 3% behentrimonnium methosulfate, about 9% cetearyl alcohol, about 2% sandal pentanol caprylate, about 3% sunflower oil, about 1.5% steramodopropyl dimethylamine, and about 1% phenoxyethanol.

18. A method of stimulating hair follicles comprising applying the composition of claim 12 topically to a subject in need thereof.

19. The compound of claim 2, wherein the compound is selected from the group consisting of: